(12) United States Patent
Mantegazza et al.

(10) Patent No.: US 7,750,177 B2
(45) Date of Patent: Jul. 6, 2010

(54) PROCESS FOR THE PREPARATION OF ENTACAPONE

(75) Inventors: Simone Mantegazza, Milan (IT); Pietro Allegrini, Milanese (IT); Gabriele Razzetti, Sesto San Giovanni (IT)

(73) Assignee: Dipharma Francis s.r.l., Baranzate (IT)

( * ) Notice: Subject to any disclaimer, the term of this patent is extended or adjusted under 35 U.S.C. 154(b) by 153 days.

(21) Appl. No.: 11/958,778

(22) Filed: Dec. 18, 2007

(65) Prior Publication Data
US 2008/0146829 A1 Jun. 19, 2008

(30) Foreign Application Priority Data
Dec. 19, 2006 (IT) .......................... MI2006A2450

(51) Int. Cl.
C07C 255/23 (2006.01)
(52) U.S. Cl. ...................................... 558/401; 558/374
(58) Field of Classification Search ................. 558/374, 558/371
See application file for complete search history.

(56) References Cited

U.S. PATENT DOCUMENTS

| | | | |
|---|---|---|---|
| 5,135,950 A | 8/1992 | Pippuri et al. | |
| 5,446,194 A | 8/1995 | Backstrom et al. | |
| 7,385,072 B2 * | 6/2008 | Venkateswarlu et al. | .... 558/401 |
| 2006/0258877 A1 | 11/2006 | Deshpande et al. | |

FOREIGN PATENT DOCUMENTS

| | | |
|---|---|---|
| WO | 2005/063693 A1 | 7/2005 |
| WO | 2005-063695 A | 7/2005 |
| WO | WO 2005063693 A1 * | 7/2005 |
| WO | 2006/064296 A1 | 6/2006 |
| WO | 2007-135406 A | 11/2007 |
| WO | WO 2007135406 A2 * | 11/2007 |

OTHER PUBLICATIONS

Xiao et al. Hebei Daxue Xuebao, Ziran Kexueban (2003), 23(2), 167-169 (CASREACT record).*
Abdel-Rhman, R. M. Indian Journal of Chemistry, Section B: Organic Chemistry Including Medicianl Chemistry (1986), 25B(8), 815-819 (CASREACT record).*
Database Beilstein, Beilstein Institute for Organic Chemistry, Frankfurt-Main, Germany, copyright 1988-2007, XP002473517. Database accession No. 601468 (Reaction ID), Abstract & Chem. Ber. 28, 1895, 2255.*
European Search Report issued in the corresponding European Application No. 07 02 3416, completed Mar. 19, 2008.
European Search Report issued in the corresponding European application No. EP 070341.6 on Mar. 19, 2008.
Database Beilstein [online] Beilstein Institute for Organic Chemistry. Frankfurt-Main DE; XP002473517, 1895.
* cited by examiner

*Primary Examiner*—Rebecca L Anderson
*Assistant Examiner*—Matthew P Coughlin
(74) *Attorney, Agent, or Firm*—Griffin & Szipl, P.C.

(57) ABSTRACT

A process for the preparation of entacapone, in particular as the polymorphic form A, comprising the preparation of a compound of formula (V),

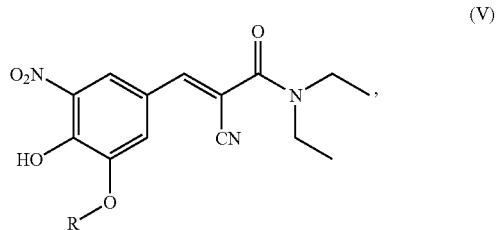

(V)

wherein R is $C_1$-$C_6$ alkyl, by condensation of N,N-diethyl-cyano-acetamide with a compound of formula (IV),

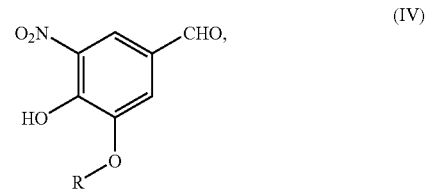

(IV)

wherein R is $C_1$-$C_6$ alkyl, in the presence of a strong basic agent; the dealkylation of the compound of formula (V) to obtain entacapone, and the crystallization thereof from methyl ethyl ketone is performed to yield the polymorphic form A. The polymorphic form A of entacapone may be used to treat Parkinson's disease and/or to enhance effectiveness of muscle control.

17 Claims, No Drawings

PROCESS FOR THE PREPARATION OF ENTACAPONE

This application claims priority from Italian Patent Application No. MI 2006A002450, filed Dec. 19, 2006, the entire disclosure of which is incorporated herein y reference.

FIELD OF THE INVENTION

The present invention relates to a novel process for the preparation of entacapone, in particular the polymorphic form A.

TECHNOLOGICAL BACKGROUND

Entacapone, namely (E)-N,N-diethyl-2-cyano-3-(-3,4-dihydroxy-5-nitrophenyl-)-acrylamide, of formula (I)

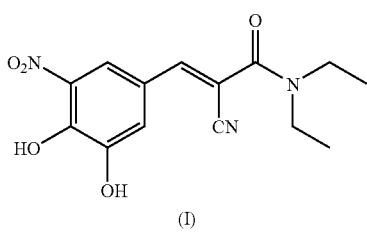

(I)

is a catechol-O-methyl-transferase (COMT) specific inhibitor, used in combination with levodopa/carbidopa in the treatment of Parkinson's disease, to enhance effectiveness in muscle control.

U.S. Pat. No. 5,446,194 discloses the preparation of entacapone according to the following Scheme 1, which involves the condensation of 3,4-hydroxy-5-nitro-benzaldehyde of formula (II) with N,N-diethylamino-cyano-acetamide of formula (III) in the presence of a catalytic amount of piperidine acetate in dry ethanol.

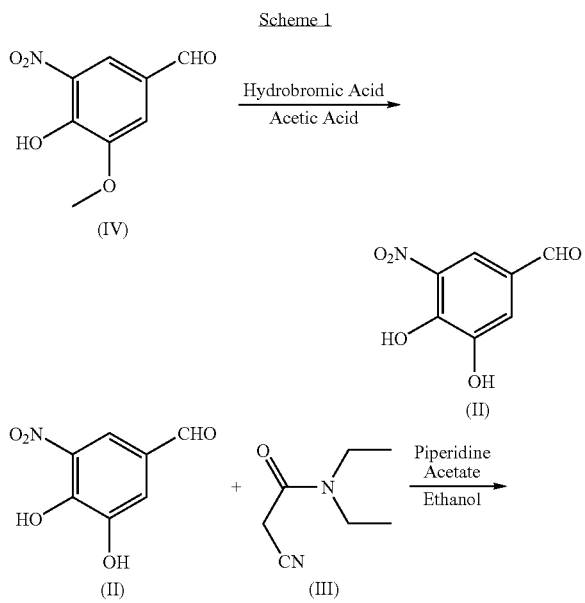

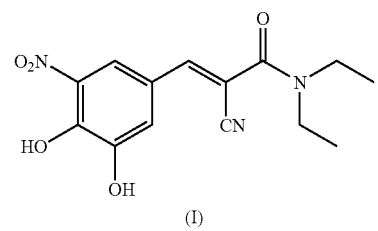

(I)

3,4-Dihydroxy-5-nitrobenzaldehyde of formula (II) is prepared from 5-nitrovanillin by demethylation with hydrobromic acid in acetic acid. Entacapone is marketed as the crystalline form A, with stereochemistry (E), known from U.S. Pat. No. 5,135,950.

According to WO 2005/063693, the preparation disclosed in U.S. Pat. No. 5,446,194 suffers from exceedingly high reaction times, of about 80-100 hours; the reactions do not go to completion and yields are not very good. Furthermore, both intermediate of formula (II) and final product require repeated purifications, due to the high instability of the catechol derivatives, that undergo oxidation when exposed to airs. The intermediate (II) in particular requires specific storage conditions, namely at a temperature of 15° C. in dark rooms.

WO 2005/063693 discloses a novel synthetic alternative to entacapone as shown in the following Scheme 2.

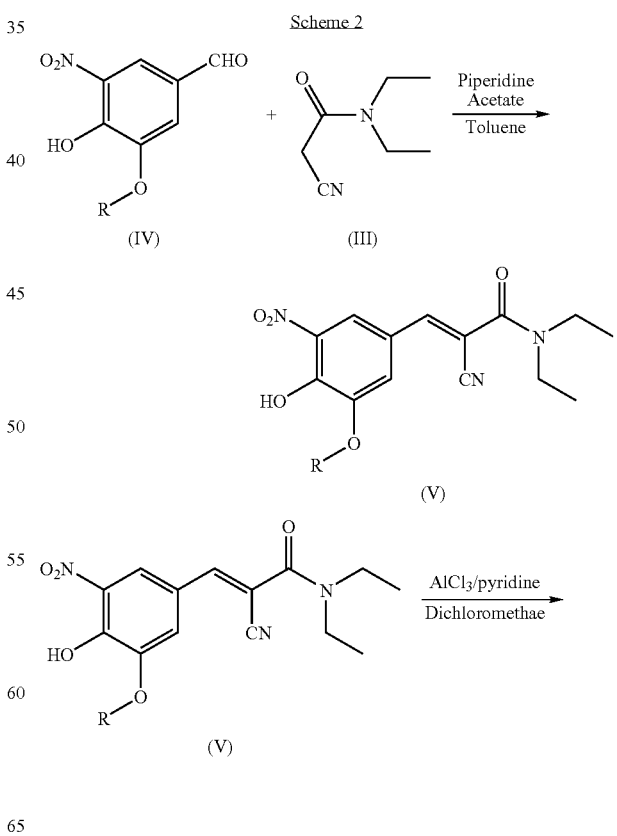

-continued

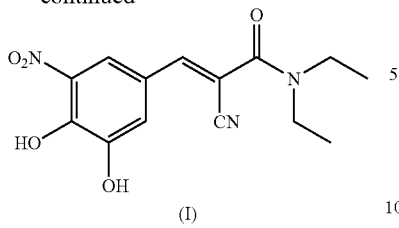

(I)

wherein R is methyl or ethyl.

This synthetic route comprises reacting a compound of formula (III) and a compound of formula (IV) in the presence of "mild acid catalysts" (literally), which according to the inventors allow to operate under conditions not aggressive towards the fragile intermediates of formula (IV) and (V). The same reference also reports that intermediate (V) is anyway highly susceptible to hydrolysis even under mild acidic or basic conditions.

However, also this synthetic approach has drawbacks that limit or make the application on an industrial scale difficult. Nitrophenol compounds of formula (IV) and (V) and entacapone itself are indeed poorly stable and the prolonged reflux of the reaction mixture at 105-110° C. involves the formation of pitches in remarkable amounts, which decreases the yield in isolated product and makes purifications of the crude compound necessary.

A further drawback of the prior art are the conditions for entacapone preparation in its crystalline form A. According to U.S. Pat. No. 5,135,950, the crystalline form A is obtained by hot dissolution and subsequent crystallization of the product from an organic acid, e.g. acetic acid, in the presence of strong mineral acids, e.g. hydrobromic acid. Such conditions have the drawback of partly degrading the final product entacapone. Moreover, the product is dried from mixtures containing organic and mineral acids, which involves industrial problems, such as long times necessary to remove the high-boiling solvents and corrosion of the drying apparatus.

WO 2006/064296 solves in part this problem by performing a crystallization from acetone in the presence of considerable amounts of acetic acid. However, the problem of purifying the final product in the presence of a high-boiling organic acid is still unsolved.

There is therefore a need for an industrially applicable process, which provides high yields, makes use of low-cost starting materials and of solvents causing low environmental impaction. Furthermore, in particular as far as the reaction temperature is concerned, the conversion reaction of intermediate of formula (IV) to intermediate of formula (V) should be carried out under milder conditions. Finally, the conditions for the crystallization of the final product should avoid the use of strong acids, high-boiling organic acids and high temperatures.

DISCLOSURE OF THE INVENTION

A synthetic process for the preparation of entacapone has now been surprisingly found, which involves both the condensation between a compound of formula (III) and a compound of formula (IV), as herein defined, and the formation of entacapone in the crystalline form A, under conditions suitable for the industrial scale.

DETAILED DISCLOSURE OF THE INVENTION

The present invention relates to a process for the preparation of N,N-diethyl-2-cyano-3-(-3-alkoxy-4-hydroxy-5-nitrophenyl-)-acrylamide, of formula (V)

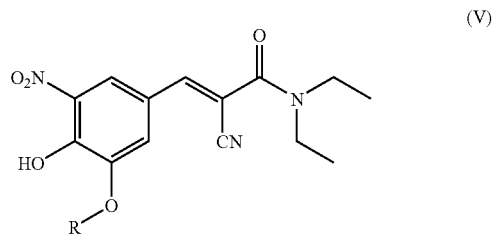

(V)

wherein R is $C_1$-$C_6$ alkyl, comprising the reaction of a compound of formula (III), namely N,N-diethyl-cyano-acetamide,

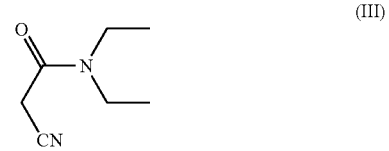

(III)

with a compound of formula (IV)

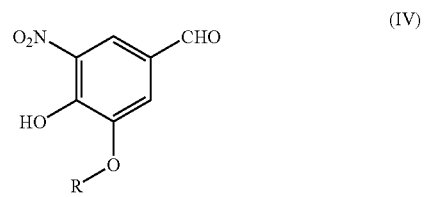

(IV)

wherein R is $C_1$-$C_6$ alkyl, in the presence of a strong basic agent.

A $C_1$-$C_6$ alkyl group, which can be straight or branched, is for example a $C_1$-$C_4$ alkyl group; in particular methyl, ethyl, propyl o tert-butyl; preferably methyl or ethyl.

Examples of strong basic agents are alkali and alkaline-earth metal hydroxides, such as lithium, sodium, potassium and calcium hydroxides; alkali and alkaline-earth metal alkoxides, such as sodium, potassium and magnesium methoxides, ethoxides, isopropoxides and tert-butoxides; and aluminium isopropoxide, preferably sodium hydroxide, potassium hydroxide and sodium methoxide; in particular sodium hydroxide.

The use of a strong basic agent to carry out the condensation is particularly surprising in that, contrary to what known in the prior art, both intermediate of formula (IV) and compound of formula (V) are stable even under strongly basic conditions.

Furthermore, it has been found that the use of a strong base to carry out the condensation of compounds of formulae (III) and (IV) allows to operate at temperatures approximately ranging from −10 to 70° C., preferably approximately from 15 to 45° C. The reaction effected under such conditions avoids protracted high temperature heating of the reaction mixtures containing instable intermediates (thermolabile) and hence their degradation.

The reaction can be carried out for example in a solvent selected from a $C_1$-$C_6$ alkanol, preferably methanol, ethanol, isopropanol, sec-butanol or n-butanol; a dipolar aprotic solvent, preferably dimethylsulfoxide, N,N-dimethyl formamide, N,N-dimethyl acetamide, or N-methyl-pyrrolidone; an ether, preferably methyl tert-butyl ether or tetrahydrofuran; a glycol, optionally partially or completely alkylated, preferably ethylene glycol, ethylene glycol mono and dimethyl ether, diethylene glycol mono and dimethyl ether or 1-methoxy-2-propanol; a chlorinated solvent, preferably methylene chloride, 1,2-dichloroethane, chlorobenzene or dichlorobenzenes; a nitrile, preferably acetonitrile; or mixtures of said solvents or mixtures thereof with water; in particular mixtures of two or three of said solvents, or mixtures of one to three of said solvents with water. Preferred solvents are methanol, ethanol and isopropanol and mixtures thereof with water.

The molar ratio of basic agent to compound of formula (IV) can approximately range from 1 to 10, preferably approximately from 1 to 2; more preferably about 1.5.

A resulting compound of formula (V) can be converted to entacapone, of formula (I)

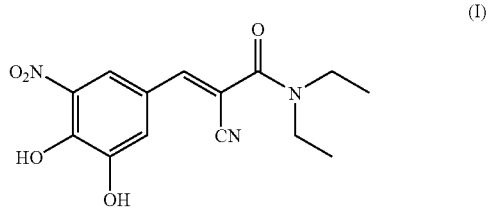

(I)

by dealkylation.

The phenol functionality in a compound of formula (V) can be dealkylated according to known methods, preferably by reaction with aluminium trichloride and a trialkylamine.

Preferred examples of trialkylamines are triethylamine, diisopropyl ethyl amine, tributyl amine; particularly preferred is triethylamine.

The reaction can be carried out, for example, in an organic chlorinated solvent, preferably dichloromethane, 1,2-dichloroethane, chlorobenzene or a dichlorobenzene; an aromatic solvent, preferably toluene or xylene; an aliphatic solvent, preferably n-hexane, cyclohexane, heptane or petroleum ether, preferably in a chlorinated or aromatic solvent; more preferably in dichloromethane or toluene.

The molar ratio of trialkylamine, particularly triethylamine, to compound (V) can approximately range from 1 to 5, preferably approximately 2.5-3.5.

The reaction can be carried out in a molar ratio of intermediate (V) to aluminium trichloride approximately ranging from 1 to 5, preferably approximately from 1 to 1.5, more preferably about 1.2.

The reaction can be conducted at a temperature approximately ranging from 0° C. to the reflux temperature of the solvent, preferably approximately from 35° C. to the reflux temperature.

The product entacapone, obtained e.g. as reported above, can be recovered in the substantially pure crystallographic form of polymorph A, by crystallization from the solvent in the absence of organic or mineral acids.

Therefore, the invention also provides a process for isolating entacapone as the substantially pure crystallographic form of polymorph A, comprising the crystallization of entacapone from methyl-ethyl-ketone (2-butanone).

The term "substantially pure crystallographic form of polymorph A" as herein used means that the polymorphic form A of (E)-N,N-diethyl-2-cyano-3-(-3,4-dihydroxy-5-nitrophenyl-)-acrylamide contains at most 2.5% and preferably less than 1.5% of other polymorphic forms or isomer (Z).

According to a preferred feature, said process of the invention comprises:
dissolution of entacapone in 2-butanone, and either
a) rapid cooling to about 30-40° C. to obtain a precipitate, subsequent heating to about 60° C.; stirring at about 60° C. for about an hour; subsequent slow cooling and recovery of the resulting solid; or
b) cooling to about 60° C. and seeding with crystalline germs, stirring at about 60 C for about an hour and subsequent slow cooling and recovery of the resulting solid.

Dissolution is preferably carried out by heating at the reflux temperature.

The terms rapid and slow cooling are herein meant according to the common technical practice in the art; for example a slow cooling can be carried out in about 3-4 hours or more.

The resulting solid can be recovered with one of the known techniques, such as filtration or centrifugation, preferably filtration, followed by drying under vacuum.

The resulting product has high purity level, anyway equal to or higher than 95%. The purity of the resulting entacapone is preferably higher than 99.5%, more preferably equal to or higher than 99.8%, all of the impurities (including the Z isomer) being less than 0.1%.

The cooling rate can be adjusted so as to provide entacapone of varying particle sizes, with mean (d[4,3]) volume approximately ranging from 25 to 300 μm. Moreover, the particle size can be suitably modified by means of known milling, micronization and fine grinding processes.

The following examples illustrate the invention.

EXAMPLE 1

Preparation of N,N-diethyl-2-cyano-3-(-3-methoxy-4-hydroxy-5-nitrophenyl-)-acrylamide; (V)

A suspension of 3-methoxy-4-hydroxy-5-nitro-benzaldehyde (100 g, 0.507 mol) in methanol (0.5 l) under nitrogen atmosphere at room temperature, is added with N,N-diethylamino-cyano-acetamide (142 g, 1.01 mol) and a sodium hydroxide solution (30.4 g, 0.761 mol) in methanol (0.5 l). The resulting mixture is reacted under mechanical stirring for 16 hours. After completion of the reaction, a 20% hydrochloric acid solution (0.5 l) is dropped in the mixture which is left to spontaneously cool to room temperature. The resulting product is filtered, washing with water (0.1 l for three times), then dried in the air. 155 g of product are obtained. Yield: 95%.

$^1$H-NMR (300 MHz), δ (DMS0): 8.10 (d, 1H); 7.85 (d, 1H); 7.70 (s, 1H); 3.40 (m, 4H); 1.15 (m, 6H).

EXAMPLE 2

Preparation of N,N-diethyl-2-cyano-3-(3,4-dihydroxy-5-nitrophenyl)-acrylamide (entacapone); (I)

A round-bottom flask under nitrogen atmosphere is loaded with N,N-diethyl-2-cyano-3-(-3-methoxy-4-hydroxy-5-nitrophenyl-)-acrylamide (134 g, 0.421 mol) dissolved in dichloromethane (0.65 l) and triethylamine (128 g, 1.26 mol). The solution is cooled to 0-5° C. and aluminium trichloride (67.4 g, 0.505 mol) is added in portions. After that, the mixture is refluxed for 3-4 hours, until completion of the conversion. The reaction mixture is cooled to 0-5° C., a 20% hydrochloric acid solution (0.5 l) is dropped in the mixture, which is left under stirring at room temperature for 30 minutes. The resulting solid is filtered, washing with water (0.1 l×3), and dried in a static dryer under reduced pressure at 50° C.; 126 g are obtained. Yield: 98%.

$^1$H-NMR (300 MHz), δ (DMS0) 7.90 (d, 1H); 7.75 (d, 1H); 7.60 (s, 1H); 3.40 (m, 4H); 1.15 (m, 6H).

EXAMPLE 3

Purification of N,N-diethyl-2-cyano-3-(-3,4-dihydroxy-5-nitrophenyl-)-acrylamide (Entacapone)

N,N-Diethyl-2-cyano-3-(-3,4-hydroxy-5-nitrophenyl-)-acrylamide (210 g) in 2-butanone (1.26 l) is loaded into a round-bottom flask under nitrogen atmosphere, and the mixture is refluxed, to obtain complete dissolution. The solution is cooled to 35-40° C. to precipitate the product, then heated again at 60° C. for about 1 h. The mixture is left to cool at room temperature in about 5 hours, cooled to 0-5° C. keeping this temperature for about 1 h, then filtered washing with 2-butanone cooled to 0-5° C. (2×0.15 l). The product is dried in a static dryer at 50° C. under vacuum. 190 g are obtained. Yield: 90%. The product was analyzed according to the procedures reported in U.S. Pat. No. 5,135,950 showing substantially the same physical characteristics as the polymorph A, with (E) stereochemistry, as therein described, with mean (d[4,3]) of about 210 μm.

The invention claimed is:

1. A process for the preparation of N,N-diethyl-2-cyano-3-(-3-alkoxy-4-hydroxy-5-nitrophenyl-)-acrylamide, of formula (V),

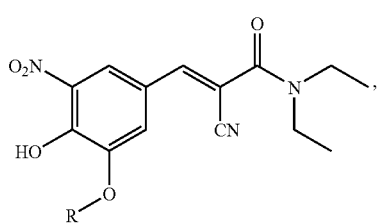

wherein R is $C_1$-$C_6$ alkyl, wherein the process comprises reaction of a compound of formula (III), namely N,N-diethyl-cyano-acetamide,

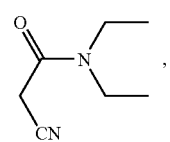

with a compound of formula (IV),

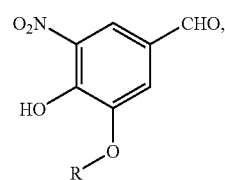

wherein R is $C_1$-$C_6$ alkyl, in the presence of a strong basic agent.

2. A process according to claim 1, wherein the strong basic agent is selected from the group consisting of an alkali or alkaline-earth metal hydroxide, an alkali or alkaline-earth metal alkoxide and aluminium isopropoxide.

3. A process according to claim 2, wherein the alkali or alkaline-earth metal hydroxide is selected from the group consisting of sodium hydroxide and potassium hydroxide.

4. A process according to claim 1, wherein the reaction is carried out at a temperature approximately ranging from −10 to 70° C.

5. A process according to claim 1, wherein the reaction is carried out in a solvent selected from a $C_1$-$C_6$ alkanol, a dipolar aprotic solvent, an ether, a glycol a glycol that is partially alkylated, a glycol that is completely alkylated, a chlorinated solvent, a nitrile or mixtures of said solvents or mixtures thereof with water.

6. A process according to claim 5, wherein the solvent is selected from methanol, ethanol, isopropanol and mixtures thereof with water.

7. A process according to claim 1, wherein the molar ratio of basic agent to compound of formula (IV) approximately ranges from 1 to 10.

8. A process for the preparation of entacapone wherein the process comprises the step of:
   dealkylation of a compound of formula (V) to obtain entacapone where the compound of formula (V) is prepared according to the process of claim 1.

9. A process according to claim 8, wherein the dealkylation is carried out by reaction with aluminium trichloride and triethylamine.

10. A process according to claim 9, wherein the molar ratio of triethylamine to compound of formula (V) approximately ranges from 1 to 5.

11. A process for isolating entacapone in a substantially pure crystallographic form of polymorph A, comprising the steps of:
   (a) dissolution of entacapone in methyl-ethyl-ketone to obtain a mixture: and
   (b) crystallization of entacapone from methyl-ethyl-ketone to obtain the substantially pure crystallographic form of polymorph A.

12. A process according to claim 8, further comprising the step of:
   crystallization of entacapone from methyl-ethyl-ketone to obtain entacapone in a substantially pure crystallographic form of polymorph A by
   i. dissolution of entacapone in methyl-ethyl-ketone to obtain a mixture;
   ii. rapid cooling of the mixture to about 30-40° C. to obtain a precipitate, and subsequent heating to about 60° C.;
   iii. stirring the mixture at about 60° C. for about an hour; and iv. subsequent slow cooling of the mixture and recovery of a resulting solid from the mixture, wherein the resulting solid is entacapone in the substantially pure crystallographic form of polymorph A.

13. A process for isolating entacapone in a substantially pure crystallographic form of polymorph A, comprising the steps of:
(a) dissolution of entacapone in 2-butanone to obtain a mixture;
(b) rapid cooling of the mixture to about 30-40° C. to obtain a precipitate, subsequent heating to about 60° C.;
(c) stirring the mixture at about 60° C. for about an hour; and
(d) subsequent slow cooling of the mixture and recovery of a resulting solid from the mixture, wherein the resulting solid is entacapone in the substantially pure crystallographic form of polymorph A,
wherein the entacapone is prepared from N,N-diethyl-2-cyano-3-(-3-alkoxy-4-hydroxy-5-nitrophenyl-)-acrylamide, of formula (V)

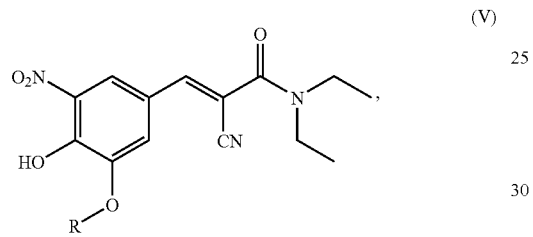

(V)

wherein R is $C_1$-$C_6$ alkyl, where the process for the preparation of entacapone comprises the steps of
(i) reaction of a compound of formula (III), namely N,N-diethyl-cyano-acetamide,

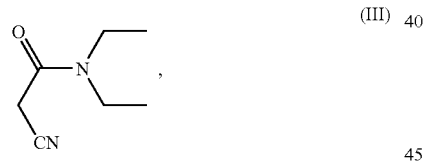

(III)

with a compound of formula (IV),

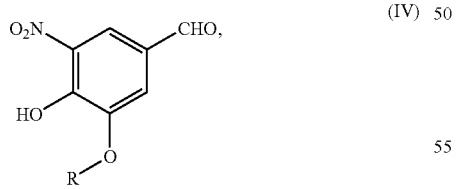

(IV)

wherein R is $C_1$-$C_6$ alkyl, in the presence of a strong basic agent; and
ii. obtaining entacapone by dealkylation of the compound of formula (V).

14. A process for isolating entacapone in a substantially pure crystallographic form of polymorph A, comprising the steps of:
(a) dissolution of entacapone in 2-butanone to obtain a mixture;
(b) cooling of the mixture to about 60° C. and seeding the mixture with crystalline germs;
(c) stirring the mixture at about 60° C. for about an hour; and
(d) subsequent slow cooling of the mixture and recovery of a resulting solid from the mixture, wherein the resulting solid is entacapone in the substantially pure crystallographic form of polymorph A,
wherein the entacapone is prepared from N,N-diethyl-2-cyano-3-(-3-alkoxy-4-hydroxy-5-nitrophenyl-)-acrylamide, of formula (V)

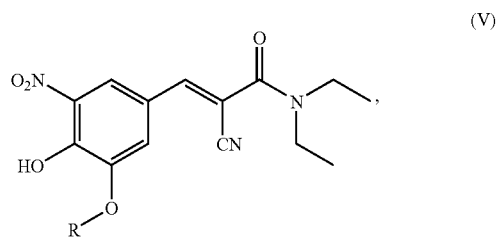

(V)

wherein R is $C_1$-$C_6$ alkyl, where the process for the preparation of entacapone comprises the steps of
i. reaction of a compound of formula (III), namely N,N-diethyl-cyano-acetamide,

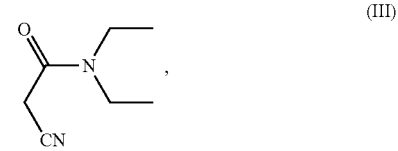

(III)

with a compound of formula (IV),

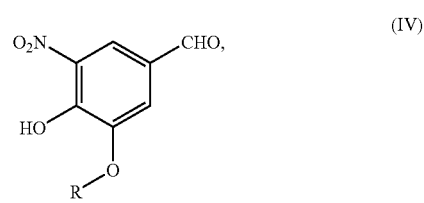

(IV)

wherein R is $C_1$-$C_6$ alkyl, in the presence of a strong basic agent; and
ii. obtaining entacapone by dealkylation of the compound of formula (V).

15. A process for isolating entacapone in a substantially pure crystallographic form of polymorph A, comprising the steps of:
(a) dissolution of entacapone in methyl-ethyl-ketone to obtain a mixture;
(b) rapid cooling the mixture to about 30-40° C. to obtain a precipitate, with subsequent heating to about 60° C.;
(c) stirring the mixture at about 60° C. for about an hour; and
(d) subsequent slow cooling of the mixture and recovery of a resulting solid from the mixture wherein the resulting solid is entacapone in the substantially pure crystallographic form of polymorph A.

16. A process for isolating entacapone in a substantially pure crystallographic form of polymorph A, comprising the steps of:
(a) dissolution of entacapone in methyl-ethyl-ketone to obtain a mixture;
(b) cooling the mixture to about 60° C. and seeding the mixture with crystalline germs;
(c) stirring the mixture at about 60° C. for about an hour; and
(d) subsequent slow cooling of the mixture and recovery of a resulting solid from the mixture wherein the resulting solid is entacapone in the substantially pure crystallographic form of polymorph A.

17. A process according to claim 8, further comprising the step of: crystallization of entacapone from methyl-ethyl-ketone to obtain entacapone in a substantially pure crystallographic form of polymorph A by
  i. dissolution of entacapone in methyl-ethyl-ketone to obtain a mixture;
  ii. cooling of the mixture to about 60° C. and seeding the mixture with crystalline germs;
  iii. stirring the mixture at about 60° C. for about an hour; and
  iv. subsequent slow cooling of the mixture and recovery of a resulting solid from the mixture, wherein the resulting solid is entacapone in the substantially pure crystallographic form of polymorph A.

\* \* \* \* \*